United States Patent
Cummings et al.

(10) Patent No.: US 6,261,788 B1
(45) Date of Patent: Jul. 17, 2001

(54) DIAGNOSTIC ASSAYS FOR INFECTIOUS PARASITIC HELMINTHS

(75) Inventors: Richard D. Cummings; Anthony Kwame Nyame, both of Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 09/400,563

(22) Filed: Sep. 21, 1999

Related U.S. Application Data

(60) Provisional application No. 60/101,197, filed on Sep. 21, 1998.

(51) Int. Cl.[7] ............... G01N 33/53; G01N 33/569; A61K 39/44; A61K 39/00
(52) U.S. Cl. ............... 435/7.22; 435/7.1; 435/975; 426/178.1; 426/184.1; 426/265.1; 426/9.1
(58) Field of Search ............... 435/7.1, 7.22, 435/975; 426/178.1, 184.1, 265.1, 9.1

(56) References Cited

U.S. PATENT DOCUMENTS 4,158,049 * 6/1979 Pelley et al. ............... 424/1

OTHER PUBLICATIONS

Nyame et al; Expression of Lex Antigen in Schistosoma Japonicum and S. Haematobium and Immune Responses to Lex Infected Animals:Lack of Lex Expression in Other Trematodes and Nematodes.Glycobiology:8 (6):615–624, 1998.*

Barsoum et al., "Diagnosis of Human Schistosomiasis by Detection of Circulating Cathodic Antigen With a Monoclonal Antibody," *J. Infect. Dis.*, 164:1010–1013, 1991.

Bergwerff et al., "The Immunologically Reactive Part of Immunopurified Circulating Anodic Antigen from *Schistosoma mansoni* Is a Threonine–linked Polysaccharide Consisting of →6)—(β–D–GlcpA–(1→) ) –β–D–GalpNAc–(1→Repeating Units," *J. Biol. Chem.*, 269:31510–316517, 1994.

Carlier et al., "Purification, Immunochemical, and Biologic Characterization of the *Schistosoma* Circulating M Antigen," 124:2442–2450, 1980.

Cummings et al., "Glycobiology of Shistosomiasis," *FASEB J.*, 10:838–848, 1996.

DeBose–Boyd, "*Schistosoma mansoni*: Characterization of an α1–3 Fucosyltransferase in Adult Parasites," *Exp. Parasitoll*, 82:1–10, 1996.

(List continued on next page.)

*Primary Examiner*—Rodney P Swartz
*Assistant Examiner*—Padma Baskar
(74) *Attorney, Agent, or Firm*—Dunlap, Codding & Rogers, PC

(57) ABSTRACT

Species of schistosoma, such as *schistosoma mansoni*, *S. japonicum* and *S. haematobium*, which infect humans and animals, synthesize the Lewis$^x$ (Le$^x$), lacdiNAc (LDN) and fucosylated LDN (LDNF) carbohydrate antigens. Parasitic helminths other than schistosomes, such as *Dirofilaria immitis* (responsible for heartworm), *Fasciola hepatica* (a liver fluke) and *Haemonchus contortus* (intestinal fluke) also synthesize the LDN and LDNF antigens, but they do not synthesize, or synthesize only undetectable amounts of, Le$^x$ antigen. The differential detection and abundance of the Le$^x$, LDN and LDNF antigens in sera and other bodily fluids of individuals is diagnostic of the presence of active and/or previous infections from schistosomes and other parasitic helminths. The present invention is directed to methods of differential detection and diagnosis of parasitic helminth infections, and kits for use in such methods.

Kang et al., "Characterization of the N–Linked Oligosaccharides in Glycoproteins Synthesized by Microfilariae of *Dirofilaria Immitis*," *J. Parasitol.*, 79(6):815–828, 1993.

1 Claim, 14 Drawing Sheets

Structures of Antigens Found in Parasitic Helminths

| Abbreviation | Structure |
|---|---|
| Le$^x$ | Fucα1-3 ↓ Galβ1-4GlcNAc-R |
| LDN | GalNAcβ1-4GlcNAc-R |
| LDNF | Fucα1-3 ↓ GalNAcβ1-4GlcNAc-R |

OTHER PUBLICATIONS

Li et al., "Visualization of P–Selectin Glycoprotein Ligand–1 as a Highly Extended Molecule and Mapping of Protein Epitopes for Monoclonal Antibodies," *J. Biol. Chem.*, 271(11):6342–6348, 1996.

Moore et al., "P–Selectin Glycoprotein Ligand–1 Mediates Rolling of Human Neutrophils on P–Selectin," *J. Cell Biol.*, 128(4):661–671, 1995.

Nash T.E., "Antibody Response to a Polysaccharide Antigen Present in the Schistosome Gut," *Am. J. Trop Med., Hyg.*, 27(5);938–943, 1978.

Nash et al., "Comparison of Four Schistosome Excretory–Secretory Antigens: Phenol Sulfuric Test Active Peak, Cathodic Circulating Antigen, Gut–Associatied Proteoglycan, and Circulating Anodic Antigen," *Am. J. Trop. Med. Hyg.*, 34(2):236–241, 1985.

Nash et al., "Further Purification and Characterization of a Circulating Antigen in Schstosomiasis," *J. of Immunol.*, 119(5):1627–1633, 1977.

Nash et al., "Antibody Response to a Polysaccharide Antigen Present in the Schistosome Gut," *Am. J. Trop. Med. Hyg.*, 27(5):944–950, 1978.

Nyame et al., "Rodents Infected with *Schistosoma mansoni* Produce Cytolytic IgG and IgM Antibodies," *Glycobiology*, 7(2);207–215, 1997.

Nyame et al., "*Schistosoma mansoni* Infection in Humans and Primates Induces Cytolytic Antibodies to Surface $Le^x$ Determinants on Myeloid Cells," *Exp. Parasitol.*, 82(0024):191–200, 1996.

Nyame et al., "*Schistosoma manson* Synthesizes Glycoproteins Containing Terminal O–Linked N–Acetylglucosamine Residues," *J. of Biol. Chem.*, 262(17):7990–7995, 1987.

Nyame et al., "Characterization of the N– and O–Linked Oligosaccharides in Glycoproteins Synthesized by *Schistosoma Mansoni* Schistosomula," *J. Parasitol.*, 74(4):562–572, 1988.

Nyame et al., "Charaterization of the High Mannose Asparagine–Linked Oligosaccharides Synthesized by *Schistosoma mansoni* Adult Male Worms," *Mol. Biochem. Parasitol.*, 28:265–274, 1988.

Nyame et al., "Complex–Type Asparagine–Linked Oligosaccharides in Glycoproteins Synthesized by *Schistosoma mansoni* Adult Males Contain Terminal β–Linked N–Acetylgalactosamine," *J. of Biol. Chem.*, 264(6):3235–3243, 1989.

Srivatsan et al., "The Human Blood Fluke *Schistosoma mansoni* Synthesizes Glycoproteins Containing the Lewis X Antigen," *J. of Biol. Chem.*, 267(28):20196–20203, 1992.

Srivatsan et al., "*Schistosoma mansoni* Synthesizes Novel Biantennary Asn–linked Oligosaccharides Containing Terminal β–linked N–acetylgalactosamine," *Glycobiology*, 2(5);445–452, 1992.

Srivatsan et al., "Demonstration of a Novel UDPGaIN-Ac:GLcNAc β1–4 N–Acetylgalactosaminyl Transferase in Extracts of *Schistosoma Mansoni*," *J. Parasitol.* 80(6):884–890, 1994.

van Dam et al., "The Immunologically Reactive O–linked Polysaccharide Chains Derived from Circulating Cathodic Antigen Isolated from the Human Blood Fluke *Schistosoma mansoni* Have Lewis X as Repeating Unit," *Eur. J. Biochem.*, 225:467–482, 1994.

Yan et al., "Immobilized *Lotus tetragonolobus* Agglutinin Binds Oligosaccharides Containing the $Le^x$ Determinant," *Glycoconj. J.*, 14:45–55, 1997.

Nyame et al., "Expression of LeX Antigen in Schistosoma japonicum and S. haematobium and Immune Response to LeX in INfected Animlas: Lack of LeX Expression in Other Trematodes and Nematodes," *Glycobiology*, Abstract XP002125650, 1998.

PCT International Search Report, App. No. PCT/US99/22028, 3 pages, Dec. 28, 1999.

* cited by examiner

Fig. 1  Structures of Antigens Found in Parasitic Helminths

| Abbreviation | Structure |
|---|---|
| Le$^x$ | Fucα1-3 → Galβ1-4GlcNAc-R |
| LDN | GalNAcβ1-4GlcNAc-R |
| LDNF | Fucα1-3 → GalNAcβ1-4GlcNAc-R |

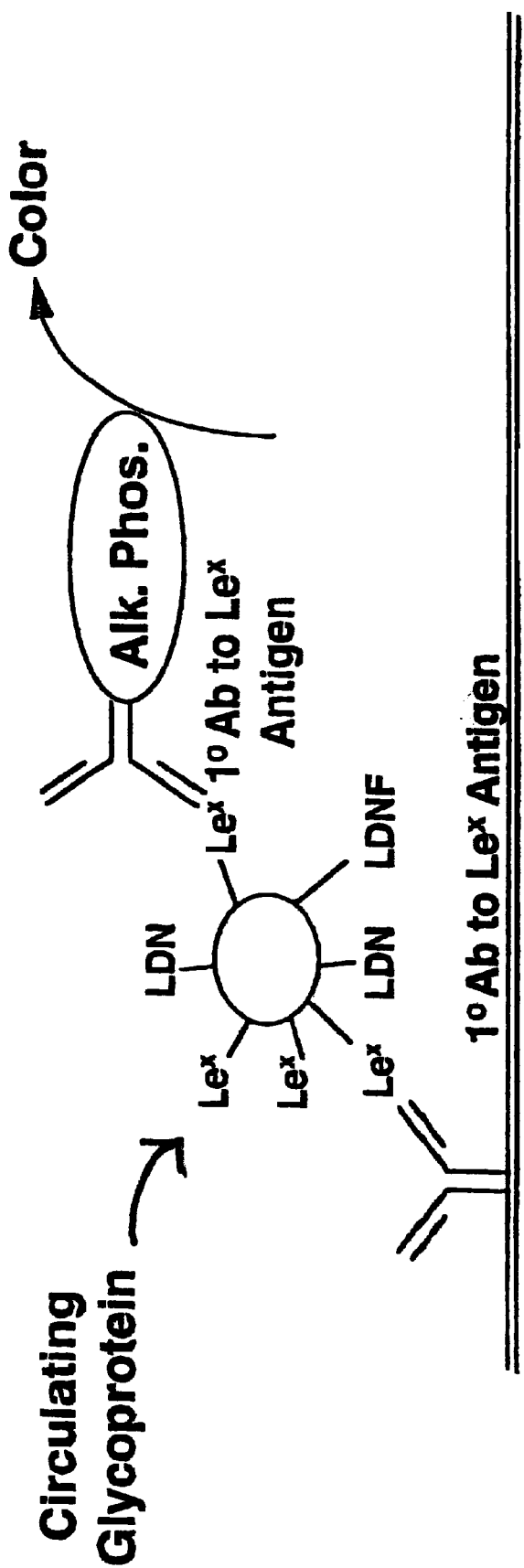
Fig. 2. Test for Circulating Glycoproteins from Helminths Containing Le$^x$ Antigen

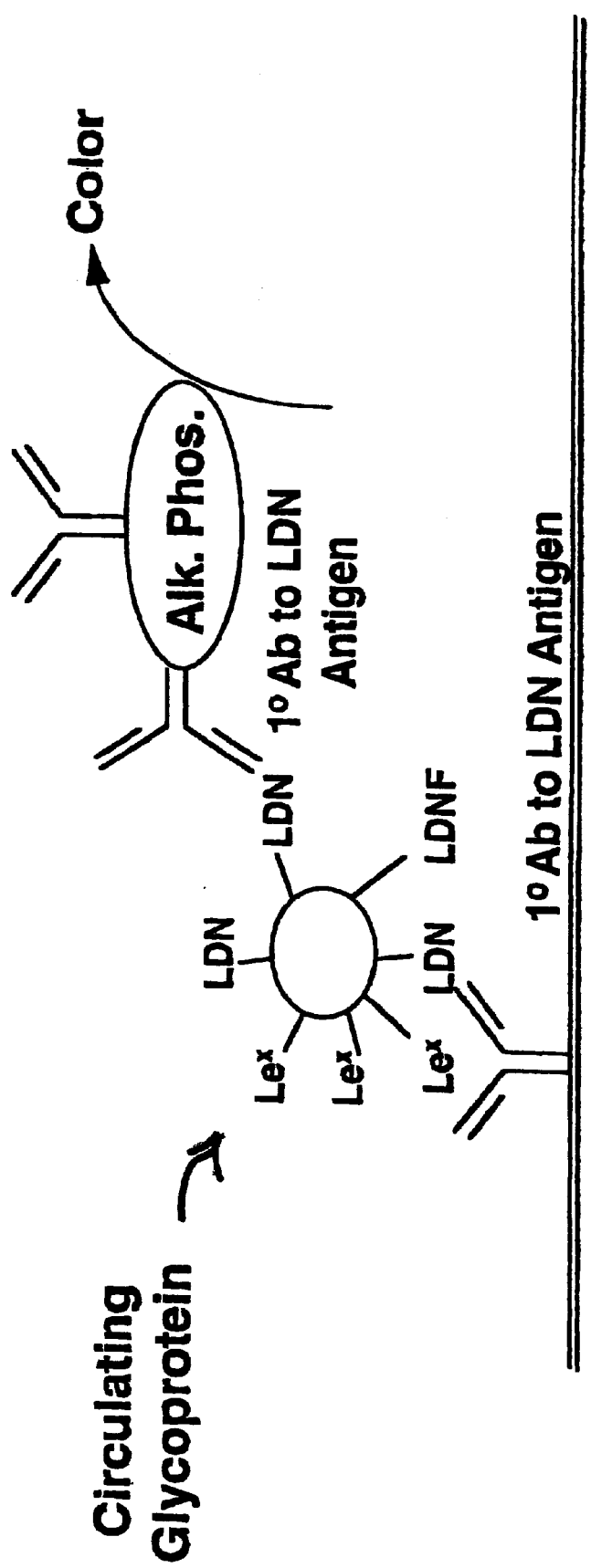
Fig. 3. Test for Circulating Glycoproteins from Helminths Containing LDN Antigen

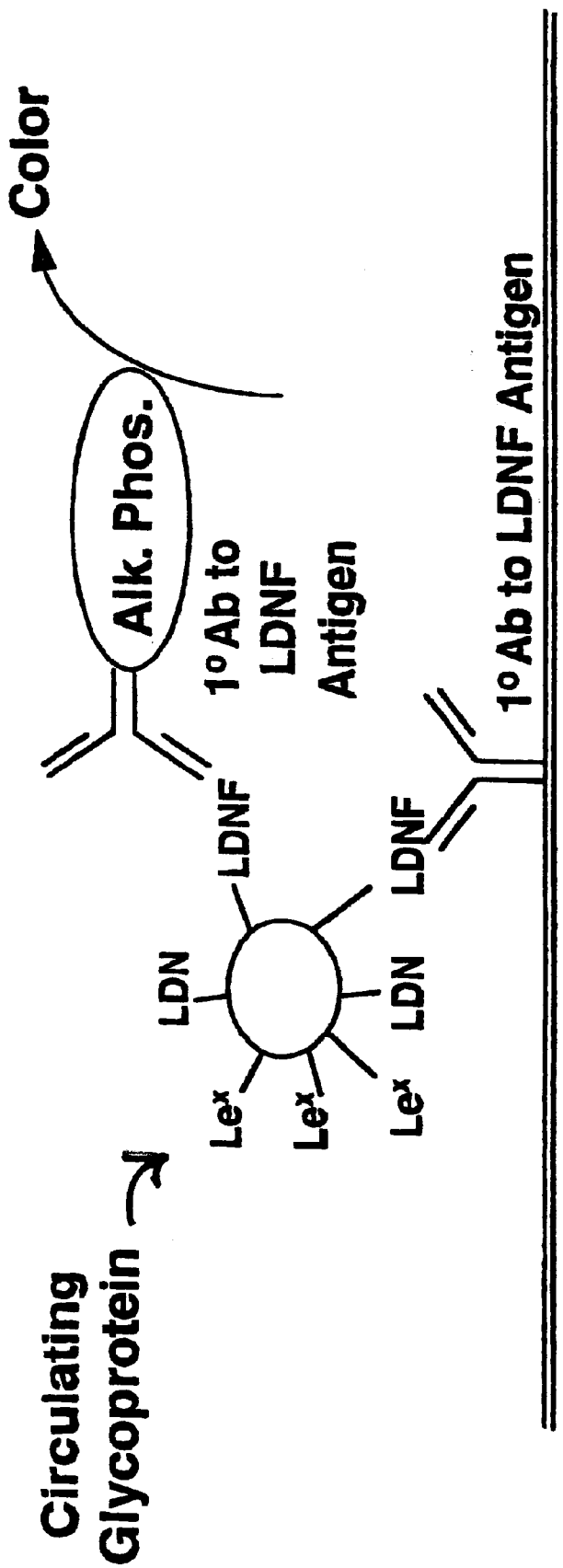
Fig. 4. Test for Circulating Glycoproteins from Helminths Containing LDNF Antigen

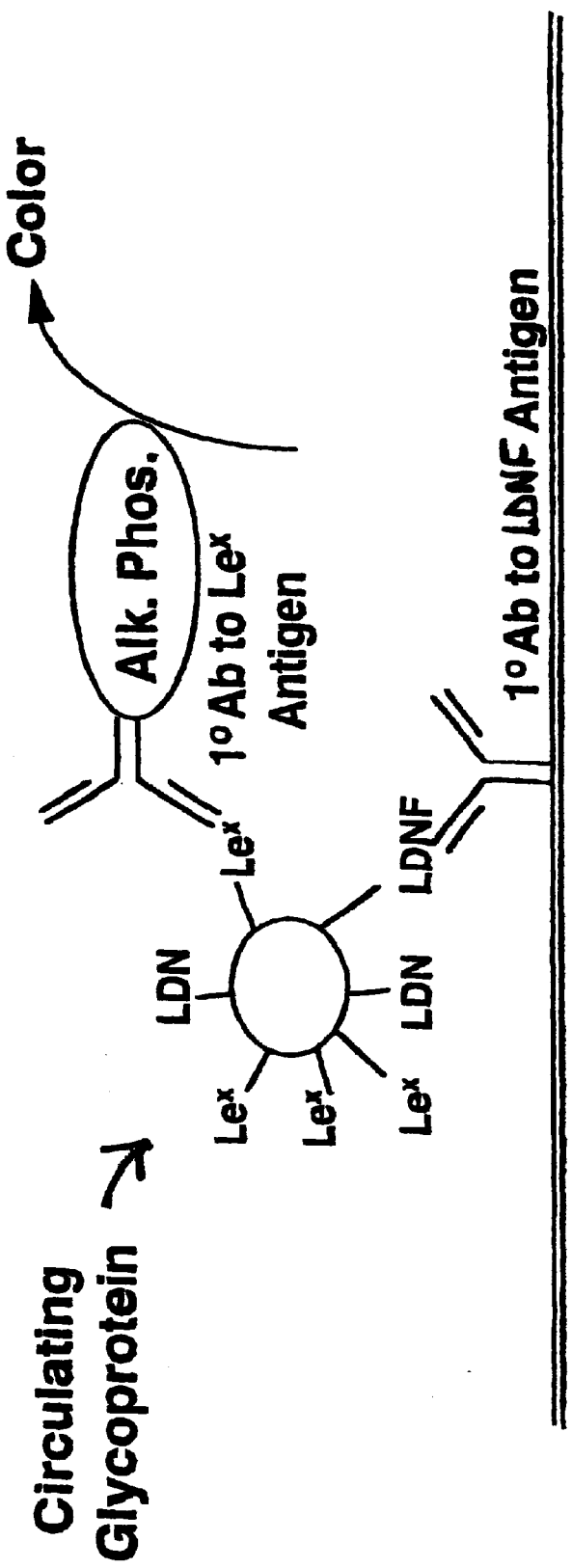
Fig. 5. Test for Circulating Heterologous Glycoproteins from Helminths Containing Le$^x$, LDN and/or LDNF Antigen

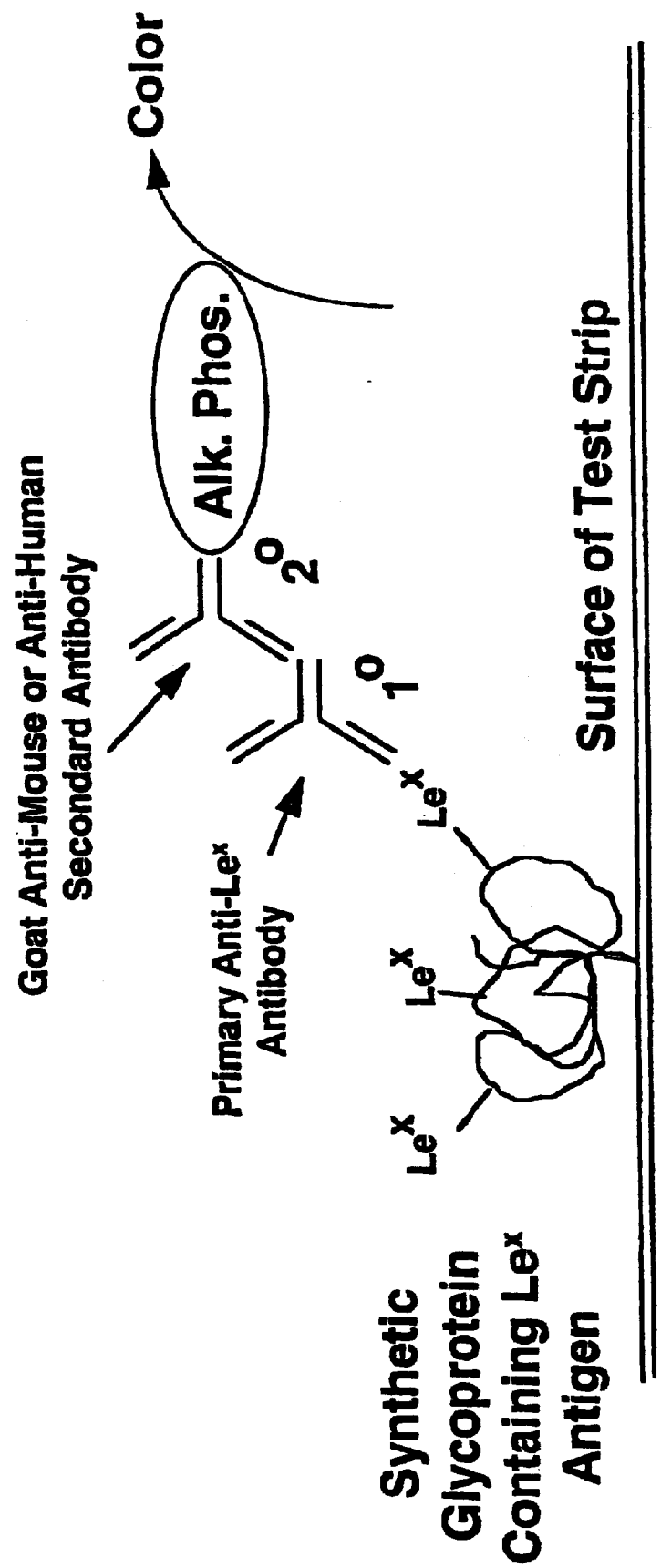
Fig. 6. Test for Circulating Anti-Le^x Antibody

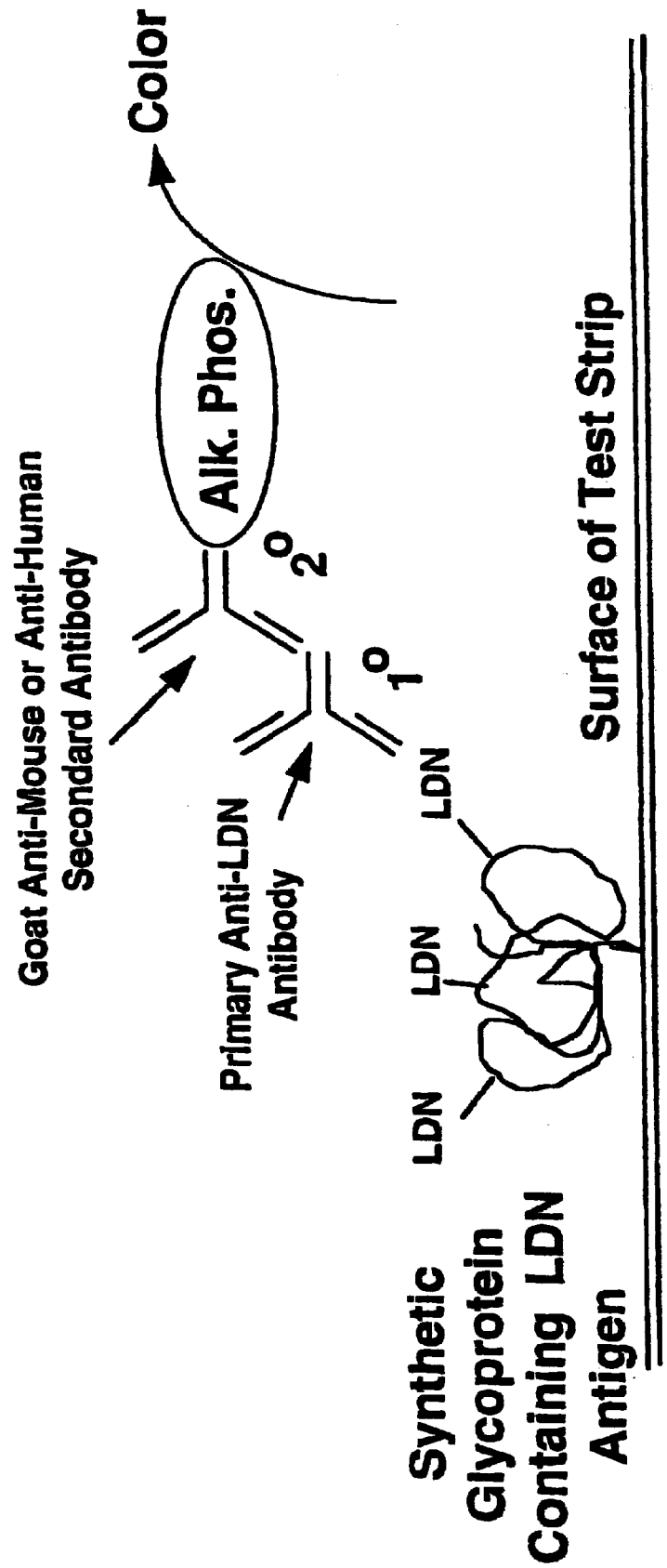
Fig. 7. Test for Circulating Anti-LDN Antibody

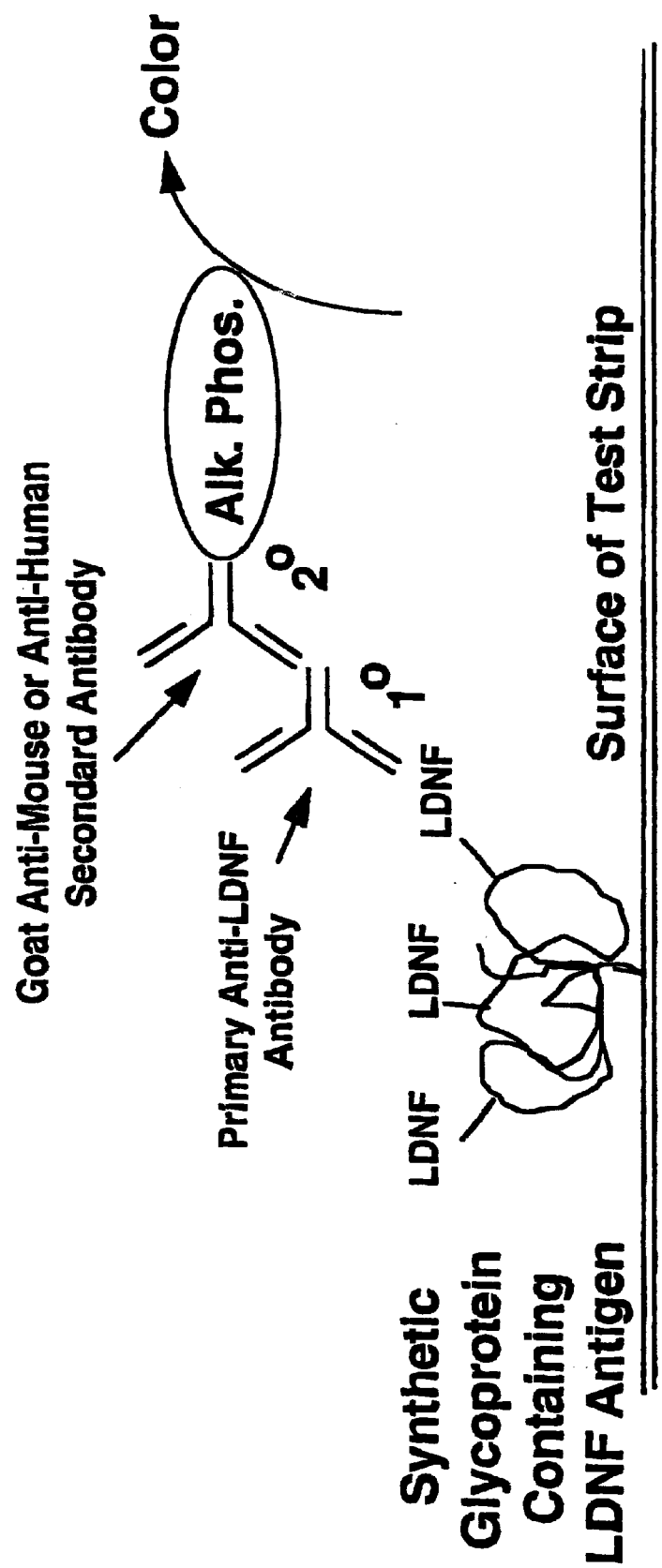
Fig. 8. Test for Circulating Anti-LDNF Antibody

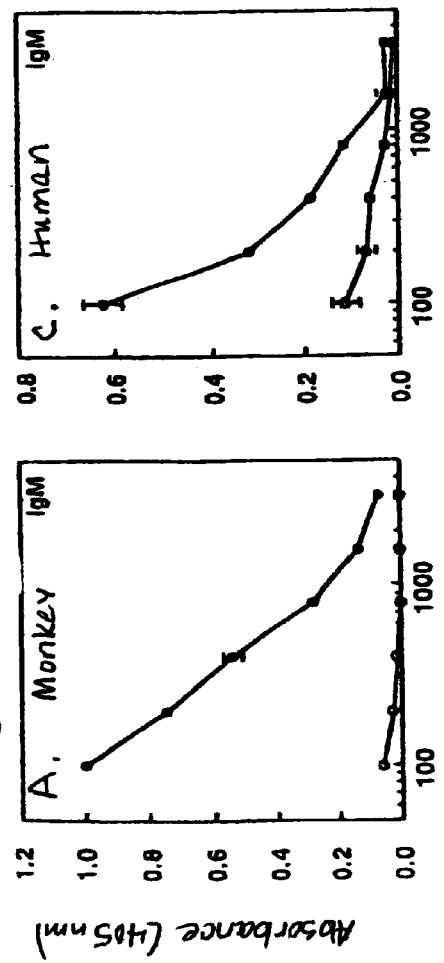
Fig. 13A
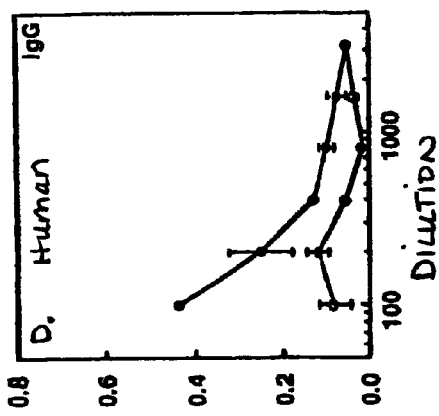
Fig. 13C
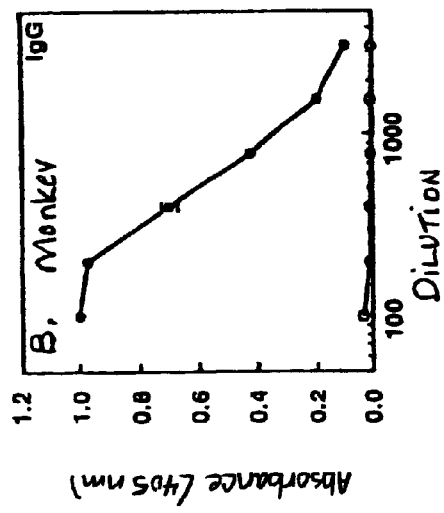
Fig. 13B
Fig. 13D

DIAGNOSTIC ASSAYS FOR INFECTIOUS PARASITIC HELMINTHS

CROSS-REFERENCE TO RELATED APPLICATIONS

The present application claims the benefit of U.S. Provisional Application Ser. No. 60/101,197, filed Sep. 21, 1998, which is hereby incorporated herein by reference.

BACKGROUND

Schistosomiasis is a vascular parasitic disease in humans caused by blood flukes of the schistosoma species. The disease afflicts an estimated 200 million people worldwide with approximately 500–600 million people at risk of infection. Schistosomiasis is one of many helminthic diseases infecting over a billion people worldwide. These diseases include ascariasis, trichuriasis, enterobiasis, filariasis, trichinosis, onchocerciasis, fascioliasis, and cysticercosis. Schistosomiasis ranks second to malaria as a major cause of morbidity and suffering due to parasites.

The means of detecting parasitic helminthic infections in general is highly variable. Some methods rely on direct detection of eggs or parasitic debris in feces and urine. This is exemplified by diagnostic procedures for Taenia saginata, Hymenolepsis nana, Diphyllobothrium latum, Schistosoma species, Fasciola hepatica, Trichuris trichiura, Gastrodiscoides hominis, Ascaris lumbricoides, common hookworms (Necator americanus, Ancylostoma duodenale, and A. ceylanicum). In some diseases diagnosis is based on examination of blood or skin scrapings and direct microscopic identification of parasites, such as for the filarial parasites, Wuchereria bancrofti, Brugia malayi and Onchocerca volvulus. Immunological and serological tests are sometimes also used for certain parasitic helminths, and they can be effective in aiding the diagnosis. Serological tests are used, for example, in diagnosis of Visceral Larva Migrans or VLM (a syndrome caused by migrating larvae of *Toxocara canis* and *T. cati*), *Trichinella spiralis*, and some filarial parasites mentioned above.

Thus, specific immunological assays for diagnosis and treatment are not common and when available, the specific antigens used for immunological detection are not chemically defined. In addition, the serological tests may provide falsely positive information about the presence of active infections, since prior infection may result in positive serological tests, due to prior immunization by parasite-derived antigens.

There is no vaccine to prevent schistosomiasis (or any other major human parasitic infection), although patients suffering from schistosomiasis can be effectively treated in most cases with certain schistosomicides to eliminate the existing infection. However, re-infection in endemic areas is common, and there is evidence for the development of drug-resistant schistosome strains. It is hoped that the availability of the modern tools of biochemistry, immunology, and cell and molecular biology will foster new developments that are needed to facilitate the production of new diagnostic assays, effective vaccines and preventatives, interventional strategies and new therapeutics. In addition, basic information learned about these parasites may have added benefits and may shed light on fundamental molecular mechanisms regulating human immunity and inflammation.

Background on Schistosome Biology

Schistosomes are dioecious and digenetic trematodes of the family Schistosomatidae and over 85 species of *schistosomes* exist. The life cycle alternates between a definitive vertebrate host and an intermediate freshwater snail host. Mammals are infected by schistosome of the genus Schistosoma, whereas birds are infected by several related genera (e.g., Ornithobilharzia and Austrogbilharzia). (The so-called "swimmers itch" in people is caused by transient skin infection with bird schisotosomes, although no permanent infection is generated.) Three of the major species that infect humans are *S. mansoni, S. japonicum and S. haematobium*. Adult schistosomes (~0.5–1.5 cm in length) dwell as pairs of males and females in veins of their definitive host and each species localizes to a specific organ—*S. mansoni* in the portal veins draining the large intestine, *S. japonicum* in the veins of the small intestine and *S. haematobium* in the urinary bladder plexus. Adult worms can live for many years and the females are prodigious egg layers. It is estimated that every 10 minutes *S. haematobium, S. mansoni and S. japonicum* release approximately 1, 2, and 10 eggs, respectively. The elliptically-shaped eggs range in size from 114 to 175 µm by 40 to 70 µm and have spines distinctive of each species. The worms have elongated bodies with an oral and a ventral sucker and a rough tegumental surface with numerous spiny protrusions.

The major pathology identified with schistosomiasis is associated with immune responses to the eggs. The eggs released by adult worms have several possible fates. Eggs that adhere to venule walls may cause a small blood thrombus (clot) that is slowly infiltrated by fibroblasts and overgrown by endothelial cells, which may be stimulated to proliferate. Non-adherent eggs may be swept back to the liver where they lodge in the hepatic capillary bed where they can cause hepatosplenomegaly and portal hypertension. If the adherent eggs successfully penetrate the vessels that lie close to the gut or bladder they may enter the feces or urine. About ⅔ of the eggs fail to penetrate completely and become lodged in the gut and bladder walls. Eggs trapped within the liver and other tissues induce granulomatous response that are largely cell-mediated immune responses to secreted egg antigens, including glycoproteins. Egg secretions produced partly by the developing miracidia exit through micropores in the eggshell and proteins, glycoproteins, and polysaccharides in these secretions elicit immune/inflammatory responses in the definitive host.

Those eggs exiting in the urine and feces of the vertebrate definitive host hatch in freshwater into miracidia that infect specific snail intermediate hosts to continue the life cycle. In the snails the replicative stage occurs asexually and eventually free-swimming cercariae are released into the surrounding water upon appropriate stimuli, such as light. Cercariae have a bifurcated tail (~200 um) and a body (~125 um) containing oral and ventral suckers important for attachment to the skin of definitive hosts. Free-swimming cercariae seek the skins of warm-blooded animals and bind the skin and attach through their oral sucker. The cercariae then contract and copious amounts of mucus are secreted from the postacetabular glands onto the skin surface. The cercariae penetrate the skin and lose their tail through violent shaking and then undergo a phenomenal transformation into a schistosomula, in which there is a rapid change from aerobic to anaerobic metabolism. The transformation is also accompanied by pronounced changes in shape of the parasite and expression of surface glycoconjugates, and loss or exposure of many surface glycoproteins within hours. The schistosomula eventually leave the skin, some enter the peripheral circulation and are swept to the heart, whereas others may enter the lymphatic system and exit via the thoracic duct. The schistosomula have an arduous and complex migration with the vertebrate hosts over a period of many days, moving through the lung and liver, until they finally come to reside in the systemic circulation. There the worms sexually mature, male and female pairing occurs and egg laying commences within 4–5 weeks.

Pathology Associated with Schistosomiasis

Schistosomiasis can cause profound pathology in infected humans and animals. The acute phase, coinciding with the onset of egg-laying, is characterized by fever, dysentery, allergic reactions with occasional abdominal pain and liver tenderness, and severe eosinophilia, which may be followed by leukopenia. Acute schistosomiasis caused by *S. japonicum* is often accompanied by severe symptoms including fevers and chills (Katayama fever) Chronic schistosomiasis arises slowly and is accompanied by pathological changes in affected organs. Organ damage can result from the T cell-mediated granulomatous response to the eggs. In *S. mansoni* and *S. japonicum* infections there is often portal hypertension and gross enlargement of the liver and spleen and in some cases there may be pipestem fibrosis of the liver. In *S. haematobium* infections there is often terminal hematuria and sometimes dysuria. Also, in *S. haematobium* bladder cancer may occur as a secondary consequence.

Diagnosis of Schistosomiasis

The most common way to diagnose schistosomiasis is identifying eggs in urine and stool samples. The numbers of eggs and the egg morphology can be used to estimate approximate numbers of egg-laying worm pairs in the individual and to identify the species of schistosome causing the infection, respectively. This assay, however, has many drawbacks. It is laborious, requires collection and handling of stool samples, and requires skilled personnel using microscopic examination. In addition, stool samples from individuals with light to moderate infections may appear negative. A second method to diagnose schistosomiasis is the presence of hematuria in urine samples, caused by *S. haematobium*. Of course, this latter diagnostic assay is specific only for this species. Some serologic and immunologic assays have been developed, generally based on egg-derived antigens, but these have generally failed to demonstrate the necessary specificity and sensitivity. There is some promise shown in immunologic assays based on detecting circulating glycoproteins in the blood of schistosome-infected animals (van Lieshout et al, 1995; 1997). However, in some published studies these assays have demonstrated specificity and sensitivity ranging around 50° in both parameters (van Lieshout et al., 1995); in some studies sensitivity was only 20% (de Jonge et al, 1990). Unfortunately, none of these immunologic assays are commercially available and it is not possible to compare one assay to another. Clearly, it is desirable to develop more specific and sensitive assays that can also discriminate between different helminthic infections.

Treatments of Schistosomiasis

Most cases of schistosomiasis can be effectively cured by single dose treatment with the common platyhelminthicide praziquantel (Biltricide). Metrifonate (Bilarcil) may be more effective for specifically treating *S. haematobium* infections. The mechanisms of killing by these drugs are not well understood. Praziquantel causes increased expression of surface antigens, along with other biochemical effects, but the drug appears to be effective in killing parasites only when there is associated humoral immunity. Some of the major targets for praziquantel killing in association with humoral immunity are surface glycoproteins.

Expression of Le$^x$ and LDN—Related Glycans by Schistosomes and Host Immunity to the Parasite It has long been appreciated that glycoconjugates derived from *schistosome cercariae*, adult worms and eggs are major antigens in infected hosts. Among the first parasite glycoconjugates identified as immunogenic were the circulating glycoproteins derived from gut of the schistosome (Nash, 1978; Nash et al., 1978; Deelder et al., 1980; Carlier et al., 1980). These glycoconjugates are designated the circulating anodic antigen (CAA) and the circulating cathodic antigen (CCA), the latter of which was originally identified as a proteoglycan-like molecule (Nash et al., 1977; Nash and Deelder, 1985).

Despite the acknowledged importance of schistosome glycoconjugates to the host immune response, it has only been in the past few years that detailed structures of schistosomal glycoconjugates have been defined, and our laboratory has been instrumental in developing this area. Many of the complex-type N-glycans in schistosome adult surface glycoproteins contain the Lewis x (Le$^x$) and polyLe$^x$ antigens (Srivatsan et al., 1992a) and Le$x$ antigen is also present in the secreted circulating cathodic antigen (CCA) (van Dam et al., 1994). These Le$^x$-containing glycans are particularly important, since we found that sera from infected animals contains a high level of antibody of both IgG and IgM to the Le$^x$ antigen (Nyame et al., 1996, 1997).

Some of the schistosome-derived N-glycans contain the lacdiNAc (LDN) sequence GalNAc$\beta$1→4GlcNAc-R (Srivatsan et al., 1992b), which contrasts with the typical Gal-GlcNAc or LacNAc sequence (Neeleman et al., 1994). LDN and LDNF (GalNAc$\beta$1→4[Fuc$\alpha$1→3]GlcNAc-R) have been found in glycoproteins synthesized by dog heart worm *Dirofilaria immitis* (Kang et al., 1993) and in the intestinal nematode Haemonchus contortus (DeBose-Boyd et al., 1998). (Gal=galactose; Fuc=fucose; GlcNAc=N-acetylglucosamine; GalNAc=N-acetylgalactosamine).

A test for diagnosing parasitic helminth infections which is highly specific, especially for schistosoma species would be highly desirable.

SUMMARY OF THE INVENTION

Expression of the Le$^x$ antigens and immunity to Le$^x$ antigens occurs in schistosomes and schistosome-infected individuals, respectively, among parasitic and non-parasitic helminths. Conversely, parasitic types of helminths express LDN and structurally-related glycans, such as LDNF and do not express Le$^x$ antigens. These results have enabled rapid and specific immunological based assays for the differential diagnosis of schistosomiasis and other helminthic infections, such as filariasis and intestinal nematode infections. These new assays will facilitate the management and treatment of the diseases and epidemiological studies of helminthic infections in the field.

DESCRIPTION OF THE DRAWINGS

FIG. 1 shows the chemical formulas of Le$^x$, LDN and LDNF.

FIG. 2 is a schematic of a test for circulating Le$^x$ antigens.

FIG. 3 is a schematic of a test for circulating LDN antigens.

FIG. 4 is a schematic of a test for circulating LDNF antigens.

FIG. 5 is a schematic of a test for circulating glycoproteins heterologous for Le$^x$, LDN and LDNF antigens.

FIG. 6 is a schematic of a test for circulating anti-Le$^x$ antibodies.

FIG. 7 is a schematic of a test for circulating anti-LDN antibodies.

FIG. 8 is a schematic of a test for circulating anti-LDNF antibodies.

FIG. 13 shows analysis of anti-Le$^x$ in sera of *S. mansoni* infected humans and rhesus monkeys. Sera from *S. mansoni* infected rhesus monkeys (A and B) or humans (C and D) were diluted 1:100, 1:200, 1:400, 1:800, 1:1600, 1:3200, 1:6400 and incubated with LNFPII-BSA (closed circles) or LnnT-BSA (open circles) in microtiter wells. Bound antibodies were detected using either goat anti-human IgM alkaline phosphatase conjugate or goat anti-human IgG alkaline phophatase conjugate. The plots represents averages of triplicate assays of serum from individuals.

DESCRIPTION OF THE INVENTION

Figure 9:
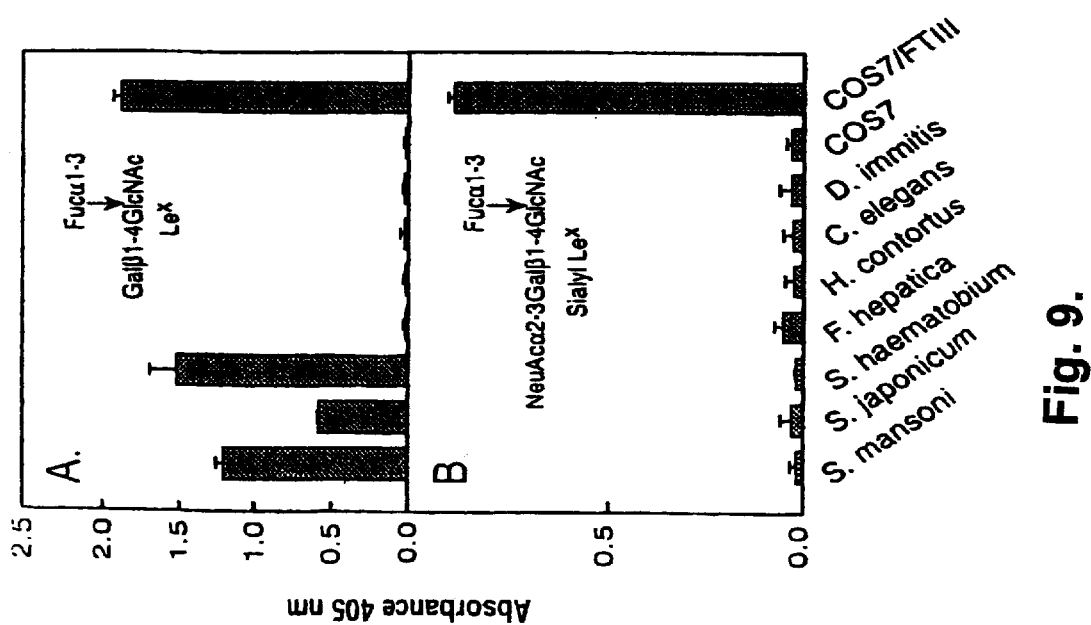
FIG. 9 shows the detection of Le$^x$ and sialyl Le$^x$ antigen expression among helminths by ELISA. Microtiter wells were coated with 10 μg/ml solution of total detergent extracts of the idicated adult trematodes and nematodes and probed for the prescence Le$^x$ and sialyl Le$^x$ and sialyl Le$^x$ antigens by ELISA using mAbs specific for Le$^x$ (A) or sialyl Le$^x$ (B). Extracts of COS7 cells were analyzed as negative controls, while extracts of S. mansoni and COSFTIV were analyzed as positive controls. Each assay was performed in triplicate and the results represent averages of the three determinations.

Schistosomiasis is a major parasitic disease affecting millions of people worldwide. It results from infections by the helminthic blood flukes, of which the primary species are *S. mansoni, S. japonicum*, and *S. haematobium*. The eggs of the parasite induce inflammatory granulomatous responses in liver, spleen and intestine that contribute the major pathological consequences of infection. There may be other pathological responses caused by secretions and autoimmune reactions to schistosomal antigens. Diagnosis of schistosomiasis and most other helminthic infections prior to the invention described herein has been rather primitive, relying on examination of urine and stool samples. As described herein, carbohydrate antigens and the glycoproteins carrying them are prime diagnostic markers for schistosomiasis and help in the differential diagnosis of schistosomiasis versus other helminthic infections. Schistosomes synthesize copious amounts of the Le$^x$ antigen Galβ1→4[Fucα1→3] GlcNAc-R (where used herein, R represents a carbohydrate, protein, or glycoprotein) on surface and secreted glycoproteins, such as the circulating cathodic antigen (CCA). Other unusual fucose-containing glycans are also present in adult worms and eggs. One new type of fucose-containing antigen is GalNAcβ1→4[Fucβ→3]GlcNAc-R, abbreviated LDNF. All schistosome species synthesize the Le$^x$ antigen on glycoproteins. Importantly, Le$^x$ expression and anti-Le$^x$ immunity is restricted to schistosomiasis and is not associated with any other common parasitic helminth, such as *Haemonchus contortus* or *Dirofilaria immitis*. Conversely, LDN and LDNF are made by schistosomes and by many other parasitic helminths. Other studies in rodents, primates and humans demonstrate that the sera of infected individuals contain both IgG and IgM antibodies reactive with Le$^x$. The anti-Le$^x$ response in schistosome-infected individuals reacts with Le$^x$ determinants on human leukocytes and can cause complement-dependent cytolysis of the cells in vitro. The presence and levels of circulating anti-Le$^x$ and schistosome-derived circulating glycoproteins expressing Le$^x$ can be used in the diagnosis and clinical management of severe disease and immune-complex formation. Thus, the combined aspects of antigens of Le$^x$, LDN and LDNF and the immune responses they evoke enable specific diagnostic assays for schistosomiasis and other helminthic diseases.

As indicated above, schistosoma species synthesize one antigen termed the Lewis$^x$ antigen (Le$^x$) (FIG. 1 where R represents a carbohydrate, a glycoprotein, or a protein) and humans and other animals infected with schistosoma species develop antibodies to this antigen. This antigen occurs on both glycoproteins and glycolipids in the adult male and female worms and their eggs. It has also been discovered that schistosome and other parasitic helminths synthesize the glycoconjugates containing the LDN and LDNF structures (FIG. 1). It has further been discovered herein that humans and other animals infected with schistosome generate antibodies to the LDN and LDNF structures. Antibodies to the LDN and LDNF structures from the sera of infected animals have been isolated and purified. Monoclonal antibodies to these structures have also been identified. Thus we now define these carbohydrate structures as antigens, as in the LDN and LDNF antigens. The fact that all parasitic helminths tested display LDN and LDNF antigens, whereas only schistosomes display the Le$^x$ antigen, allow for the development of a number of differential diagnostic assays for schistosomiasis and other parasitic helminthic infections as described below.

These assay methods are solid-phase methods schematically represented in FIGS. 2–8 employing, for example, either immobilized monoclonal antibodies to either the Le$^x$, LDN, or LDNF antigens or direct detection of the circulating antibodies to these antigens using the sera, saliva, sputum, mucus, or urine specimens from infected animals.

It will be understood by persons of ordinary skill in the art that the present invention is not limited to the use of Le$^x$, LDN, and LDNF antigens and antibodies thereto for detecting parasitic helminth infections, and specifically infections by Schistosoma species. It is contemplated that any antigen broadly characteristic of and specific to parasitic helminths, and antibodies thereto can be used in place of LDN and/or LDNF antigens and antibodies, and that any antigen specific to Schistosoma species can be used in place of the Le$^x$ antigen, or antibodies thereto as described herein.

FIGS. 2–4 depict assays wherein a monoclonal antibody to either the Le$^x$ (FIG. 2), LDN (FIG. 3), or LDNF antigen (FIG. 4) is immobilized and used to capture circulating antigen and to detect it in a manner well known to those of ordinary skill in the art. The captured antigen is detected in the assays of FIGS. 2–4 by the homologous antibody. That is in FIG. 2 anti Le$^x$ is used for capture and anti-Le$^x$ is used for detection. In FIG. 3 anti-LDN is used for capture and detection. In FIG. 4 anti-LDNF is used for capture and detection. In the assay of FIG. 5 a heterologous use of monoclonal antibodies for detecting circulating antigens is depicted. In this assay, an anti-LDNF antibody may be used for capture and an anti-Le$^x$ may be used for detection, for example. Other heterologous combinations based on the example in FIG. 5 are easily envisioned by one of ordinary skill in the art, e.g., the capture/detection combinations may be anti-Le$^x$/anti-LDN, anti-Le$^x$/anti-LDNF, anti-LDNF/anti-Le$^x$, antiLDN/anti-LDNF, or anti-LDNF/anti-LDN antibodies, or other combinations of the above.

FIGS. 6–8 depict assays in which a synthetic neoglycoprotein (or other antigen display structure) is generated using the methods developed for synthesis of the relevant carbohydrate antigen under consideration, and the immobilized neoglycoprotein containing the covalently attached antigen is used in a solid-phase format to detect the presence of circulating so-called primary antibodies to the antigen in sera, saliva, sputum, mucus, or urine specimens of potentially infected humans or animals. In these assays the primary antibody recognizing antigen is the anti-Le$^x$ (FIG. 6), LDN (FIG. 7), or LDNF (FIG. 8) that occurs in the sera of infected humans or animals, whereas a secondary antibody which binds to the primary antibody for detecting bound primary antibody is, for example, either goat-antihuman, goat-anti-mouse, goat-anti-dog, etc. depending on the source of the primary antibody. These general assays described, for example, in FIGS. 2–8 are well known to those of ordinary skill in the art and therefore further discussion of their specific construction are not deemed necessary herein.

The advantages of the assays of FIGS. 2–5 is that they detect the presence of active (current) infection, but not previous infection, due to the identification of circulating antigens derived from the living parasite that are released, secreted or sloughed from the parasite surface into the bodily fluids of the infected human or animal. The advantages of the assays of FIGS. 6–8 is that they detect the presence of a previous infection and/or immunity to the parasite, due to the generation of an immune response to the parasite-derived antigens. An advantage of the results from all assays used together is that they can identify whether an individual currently has or has had an infection by schistosoma species versus infection by another non-Schistosoma helminth species.

If the immunological response to circulating Le$^x$ antigens (e.g., FIG. 2) is negative, but the immunological response to immobilized Le$^x$ antigens (e.g., FIG. 6) is positive, the individual is considered to have had a previous infection by Schistosoma species.

If the immunological response to circulating Le$^x$ antigens (FIG. 2) is positive and the immunological response to immobilized Le$^x$ antigens (FIG. 6) is also positive, the individual is considered to have an active (current) infection by Schistosoma species.

If the immunological response to circulating Le$x$ antigens (FIG. 2) is negative, and the immunological response to immobilized Le$^x$ antigens (FIG. 6) is negative, the individual is considered to have neither an active or a recently prior infection by schistosoma species.

If the immunological response to circulating Le$^x$ antigens (FIG. 2) is negative, but the immunological responses toward LDN and/or LDNF antigens (FIGS. 3 and 4) are positive, and the immunological response to immobilized target Le$^x$ antigens (FIG. 6) is negative, but the responses toward immobilized LDN and/or LDNF (FIGS. 7 and 8) are positive, the individual is considered to not have either an active or recently prior infection by either Schistosoma species, but is considered to have an active infection by another parasitic helminth species.

If the immunological responses to circulating Le$^x$, LDN, and LDNF (FIGS. 2–4) antigens are negative, and immunological responses to immobilized Le$^x$, LDN and LDNF (FIGS. 6–8) are negative, the individual is considered not to have either an active or recently prior infection by Schistosoma species or other parasitic helminth.

If the immunological responses to circulating Le$^x$, LDN and LDNF antigens (FIGS. 2–4) are negative and the immunological response to immobilized Le$^x$ antigen (FIG. 6) is negative, but the immunological responses to immobilized LDN and LDNF antigens (FIGS. 7 and 8) are positive (i.e., LDN and LDNF antibodies are detected), the individual is considered not to have had either an active or recently prior infection by Schistosoma species but is considered to have a recently prior infection by another parasitic helminth.

Neoglycoproteins used herein are generated by incubating LDN, LDNF, and Le$^x$ (0.1 mg/ml) can with sodium cyanoborohydride and bovine or human serum albumin (1 mg/ml) in sterile conditions at room temperature for 1 week. Coupling is monitored until approximately 5 mol/mol has occurred. After coupling, the neoglycoprotein is separated from unreacted sugar by gel filtration on Sephadex G-50 columns in saline. The neoglycoproteins are sterile-filtered and stored at 10 µg/ml concentration.

In the assay format typified by FIGS. 6–8 the neoglycoprotein is immobilized on plastic microtiter plates at 10 µg/ml overnight 4° C. and then blocked with 5% BSA or HSA. Wells are incubated with serially-diluted sera (or other specimens) collected from individuals. Antibodies in sera that bind to LDN, Le$^x$, or LDNF-containing neoglycoproteins are detected by a 2° antibody of goat anti-mouse IgG or IgM-peroxidase or alkaline phosphatase, or other effective means known to those of ordinary skill in the art.

In the assay format typified by FIGS. 2–5, mAb to LDN, Le$^x$, or LDNF is immobilized by incubation in microtiter plates at 10 µg/ml as above and blocked with 5% BSA or HSA. Wells are incubated with serially diluted sera (or other specimens) collected from individuals. Captured antigens are detected by a detecting antibody to LDN, Le$^x$, or LDNF or to peptide determinants thereof. As noted above, in the assay typified by FIGS. 6–8, the antigens could be displayed using any appropriate antigen display structure known to those of ordinary skill in the art.

Where used herein, the terms "negative for Le$^x$ antigen," or "negative for antibodies to Le$^x$ antigen" or similar terms are not meant to imply that some non-Schistosoma parasitic helminths may not produce minute amounts Le$^x$ antigen, or may not induce some antibody response thereto, but that production of Le$^x$ antigen by non-Schistosoma parasitic helminths is negligible and essentially non-detectable in comparison to Le$^x$ antigen production by Schistosoma species.

Experimental

Figure 10A:
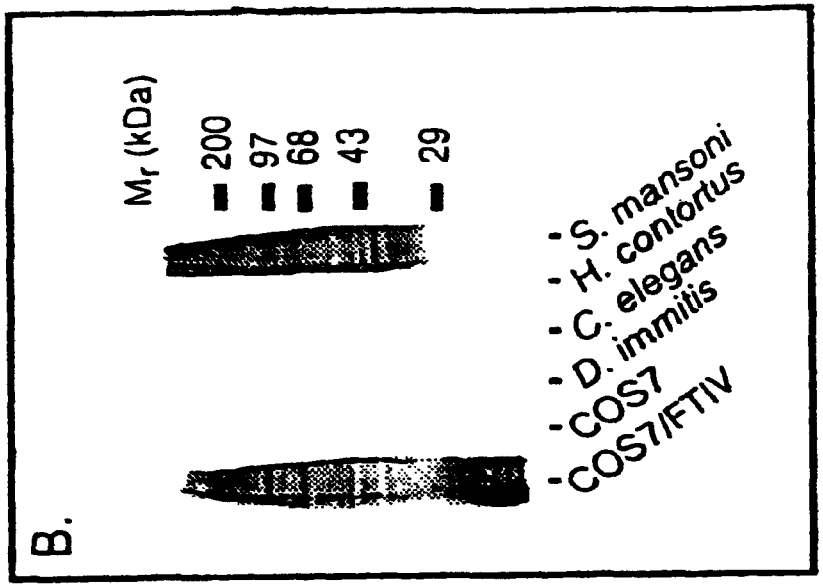
FIG. 10 shows a Western blot analysis of helminths for glycoproteins bearing Le$^x$ (A: *S. japonicum, S. haematobium, F. hepatica*; B: *D. immitis, C. elegans, H. contortus*. Extracts of the indicated trematodes and nematodes (25 μg) were separated by SDS-PAGE under reducing conditions and the presence of glycoproteins bearing Le$^x$ were identified by immunoblotting using anti-CD-15 mAb and ECL detection system. Extracts of COS7 cells were used as negative controls, while extracts of *S. mansoni* and COSFTIV were positive controls.
Figure 10B:
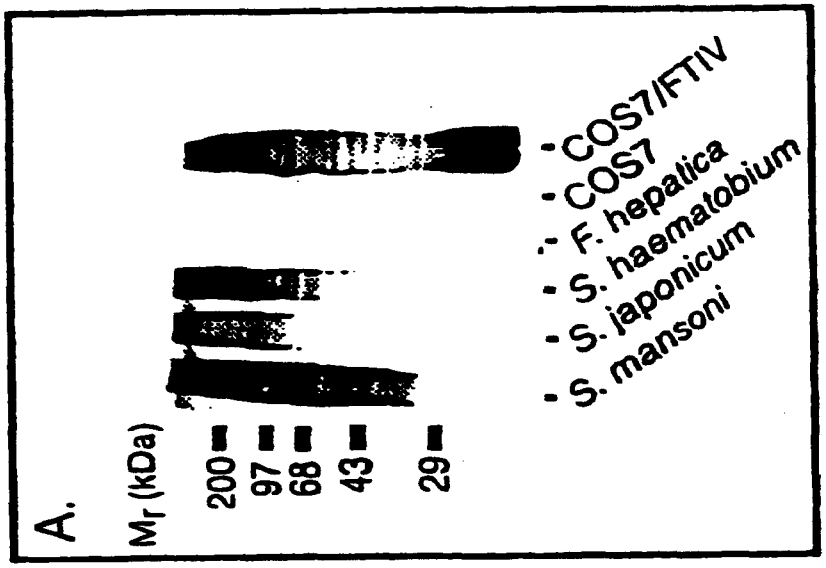
Figure 11A:
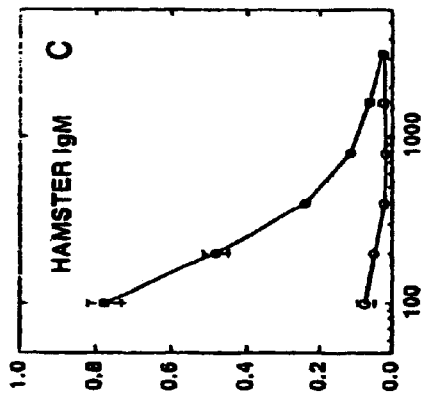
FIG. 11 shows presence of anti-Le$^x$ in sera of *S. mansoni* infected mice (A and B) and hamsters (C and D). Microtiter wells were coated with LNFPIII-BSA (closed circles) or LnnT-BSA (open circles) and incubated with sera from different infected mice or hamsters serially 1:100, 1:200, 1:400, 1:800, 1:1600, 1:3200, 1:6400. Bound antibodies were probed by incubation with alkaline phosphatase labeled goat anti-mouse IgM (A and C) or IgG (B and D), followed by incubation with p-nitrophenylphosphate substrate and optical density measurements at OD-405. Each plot is an average of triplicate experiments and represents analysis of serum from an individual mouse. Uninfected animals showed no responses in these ELISAs.
Figure 11B:
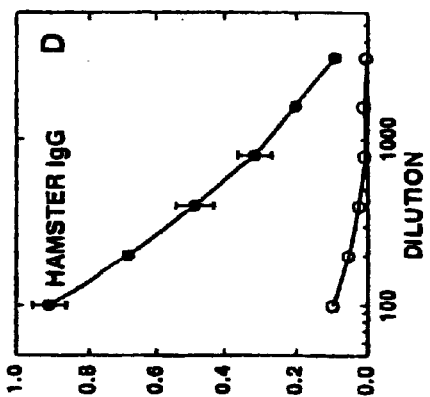
Figure 11C:
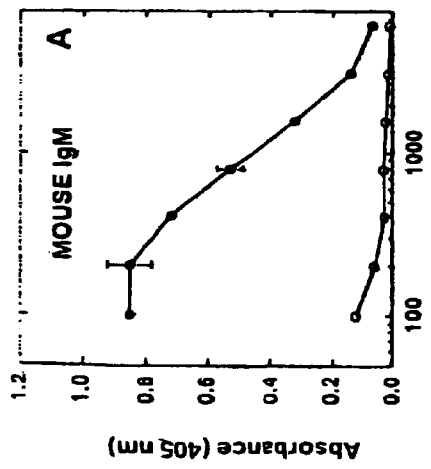
Figure 11D:
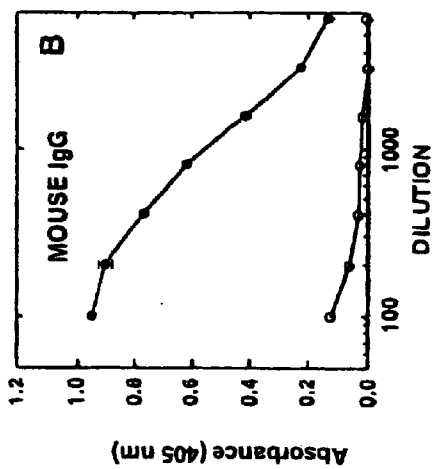

*S. mansoni, S. haematobium* and *S. japonicum* Synthesize Le$^x$ Containing Glycans, Whereas Other Helminths do not Express Le$^x$ Determinants To determine the generality of the synthesis of Le$^x$ antigens by schistosome species, extracts of *S. mansoni, S. haematobium,* and *S. japonicum* were tested both in ELISA (FIG. 9) and by Western blot analysis (FIG. 10) for the expression of Le$^x$ antigens. As shown, both techniques demonstrated that Le$^x$ expression is common to all schistosome species infecting human (FIGS. 9A, 10A). As controls, we utilized extracts from a related trematode, *Faciola hepatica*, and the nematodes *D. immitis*, and *H. contortus* and the free-living nematode *C. elegans*. The results demonstrate that other helminths did not display detectable amounts of Le$^x$ antigens in either assay format (FIGS. 9A–B, 10A–B).

Sera of Rodents Infected with *S. mansoni* Contain Both IgG and IgM Anti-Le$^x$ Antibodies The induction of antibody responses in rodents to the Le$^x$ determinants on schistosomes was investigated using 5 mice and 5 hamsters chronically infected with *S. mansoni*. Sera from 5 uninfected mice and 5 uninfected hamsters were analyzed as controls. The presence of anti-Le$^x$ antibodies in the sera of the infected rodents was detected by ELISA using LNFPIII-BSA as the target antigen. LNFPIII is a fucosylated pentasaccharide Galβ→4[Fucα1→3]GlcNAcβ1-→3Galβ1→4Glc containing a single Le$^x$ determinant. Since bovine serum albumin (BSA) is not glycosylated, it is conveniently used as a carrier to which sugars are covalently attached to generate a so-called neoglycoprotein. Control neoglycan was LnnT-BSA. Sera from each of the infected mice and hamsters contained both IgM and IgG antibodies that bound to LNFPIII-BSA and the reactivity could be detected at 1:1,600 dilution of sera (FIGS. 11A–D). Sera from uninfected animals did not bind to LNFPIII-BSA. Sera from infected hamsters also contained both IgM and IgG antibodies reactive to LNFPIII-BSA and the reactivity could similarly be detected up to 1:1,600 dilution of sera. As a control, no antibody binding was observed for either the infected or uninfected mice or hamsters when underivatized BSA was used as a target (data not shown). The subclass distribution of the IgG antibodies reacting with Le$^x$ determinants was characterized for the infected mice sera by ELISA using LNFPIII-BSA targets. Bound IgG subclasses were detected by anti-mouse subclass antibodies. LNFPIII-BSA binding IgG antibodies from all the 5 infected mice contained IgG1, IgG2a and IgG2b subclasses (data not shown). The presence of anti-Le$^x$ IgG2a and IgG2b indicates that the sera of the infected animals could mediate complement-dependent cytolysis of Le$^x$ bearing target cells. Rodents infected with *S. japonicum* and *S. haematobium* reacted similarly in the above assays, demonstrating that all the major schistosome species induce similar anti-Le$^x$ responses in infected animals (data not shown)

Figure 12:
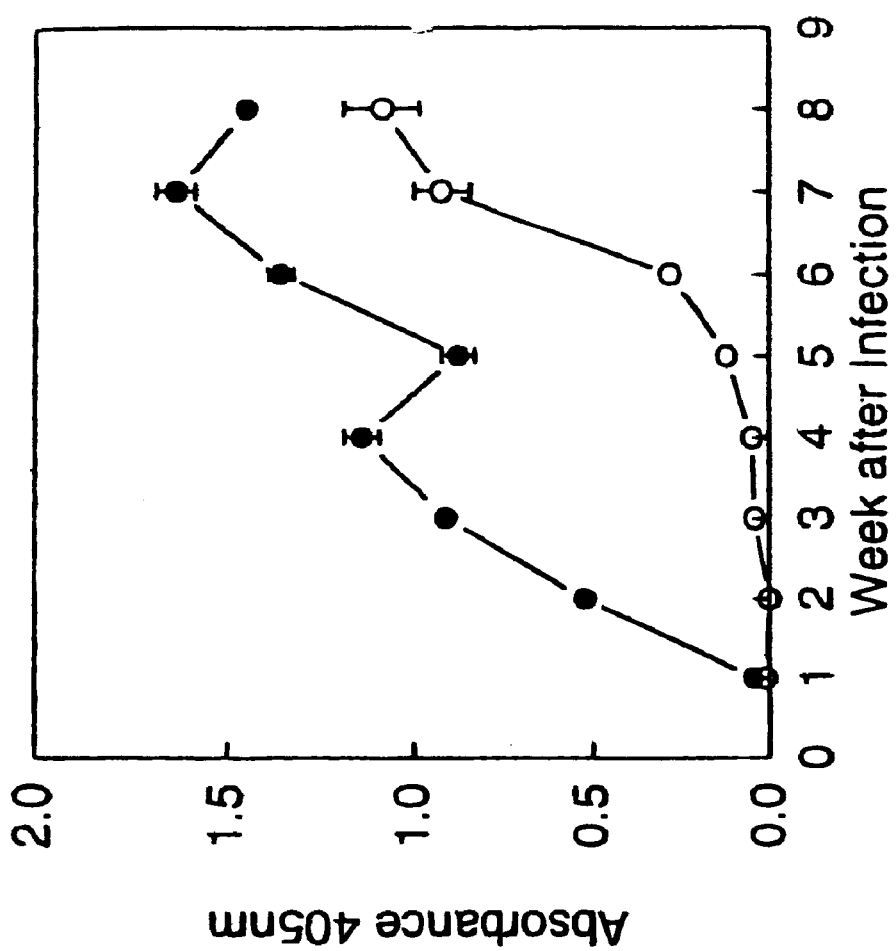
FIG. 12 shows the longitudinal study of *S. mansoni* infected mice for the appearance of anti-Le$^x$ IgM and IgG responses. Ten Swiss webster mice were infected with 250 cercariae each and bled weekly to obtain antisera. The sera were diluted 1:200 and incubated with immobilized LNFPIII-BSA in microtiter wells. Bound anti-Le$^x$ wereprobed with peroxidase-labeled goat anti-mouse IgM (closed circle) or IgG (open circle). The results shown represent the average of the absorbance for the 10 infected animals. Ten uninfected animals were similarity analyzed and no reactivity to Le$^x$ antigen was observed at any time in their sers.

Expression of Anti-Le$^x$ IgM Occurs Early in Infection (Within 2 Weeks) and Prior to Egg-Laying When the Pathology Associated with the Diseases is Manifested To determine how long it takes for infected mice to mount an IgM and IgG response to the Le$^x$ antigen, we performed a longitudinal study. Ten Swiss Webster mice were infected with 250 cercariae and 10 uninfected mice served as controls. Blood was drawn from tails each week following infection and tested for reactivity with LNFPIII-BSA in ELISA. The IgM response to the Le$^x$ antigen was detected by week 2 and peaked in a biphasic pattern at weeks 4 and 7 (FIG. 12). In contrast, the IgG response to the Le$^x$ antigen was detected at weeks 5–6 and continued to increase thereafter. No anti-Le$^x$ response was detected at any time in the 10 uninfected control mice (data not shown).

Sera of *S. mansoni*-Infected Primates and Humans Contain Both IgG and IgM Anti-Le$^x$ Antibodies The presence of anti-Le$^x$ antibodies in the sera of *S. mansoni*-infected rhesus monkeys and humans was investigated by ELISA using the neoglycoprotein, LNFPIII-BSA as target antigen. Sera used in the assays were derived from 5 *S. mansoni* infected rhesus monkeys and 5 Puerto Rican schistosomiasis patients. IgM and IgG antibodies reactive to LNFPIII-BSA were detected in the sera of all the infected rhesus monkeys and humans tested (FIGS. 13A–D). ELISA analysis of sera from 5 uninfected rhesus monkeys and 5 healthy uninfected human volunteers were negative for LNFPIII-BSA binding. Fucose in the Le$^x$ determinant was critical for antibody recognition, since antibodies in sera of infected individuals failed to bind to LNnT-BSA target antigens. LNnT lacks the fucose linked α1,3 to GlcNAc found in LNFPIII.

Figure 14:
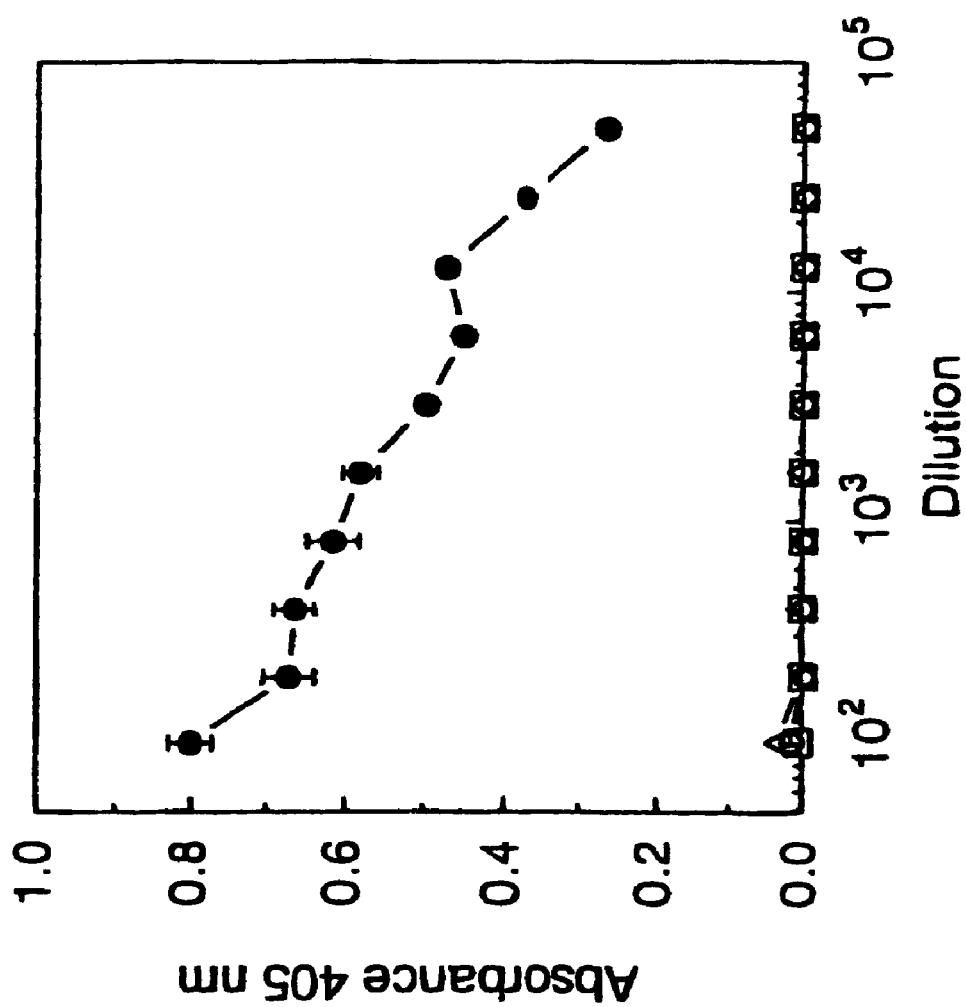
FIG. 14 shows analysis of specificity of IgM mAb, SMLEX-M3, by ELISA. Ascites fluid prepared from anti-Le$^x$ positive hybridoma derived from the spleen of *S. mansoni* infected Balb/c mice was serially diluted and analyzed for reactivity toward LNFPIII-BSA (●), LNFPII-BSA (◇) sialyl Le$^x$-BSA (⌧) and LnnT-BSA (△)by ELISA. Each ELISA was done in triplicate and the results represent averages of the three determinations.

Monoclonal Antibodies Have Been Identified From Hybridomas Derived From Spleens of Schistosome-Infected Rodents That React Specifically With Le$^x$ Antigen The discovery that *S. mansoni* infected mice produce both IgM and IgG to Le$^x$ prompted us to try and identify mAbs that recognize Le$^x$ using spleens from infected animals for the production of hybridomas. Spleens were removed from 8-wk infected animals and hybridomas produced and screened in ELISA using LNFPIII-BSA as a target. Both IgG and IgM secreting hybridomas were identified and the IgM positive clones were further investigated to obtain the needed preliminary data for this application. One mAb identified is designated SMLEX-M3. FIG. 14 illustrates the specificity of SMLSEX-M3 for Le$^x$ using a variety of carbohydrate-based target antigens. SMLEX-M3 demonstrates clear specificity for Le$^x$.

While the invention has been described above in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the previous examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

Changes may be made in the construction and the operation of the various components, elements and kits described herein or in the steps or sequences of steps of the methods described herein without departing from the spirit and scope of the invention as defined in the following claims.

Literature Cited:
1. Barsoum, I. s., Kamal, K. A., Bassilyh, S., Deelder, A. M., and Colley, D. G. (1991) *J. Infect. Dis.* 164 pg. 1010–1013.
2. Bergwerff, A. A., Van Dam, G. J., Rotmans, J. P., Deelder, A. M., Kamerling, J. P. and Vliegenthart. J. F. G. (1994) *J. Biol. Chem.* 269, pp. 31510–31517.
3. Carlier, Y., Bount, D., Strecker, G., Debray, H. and Capron, A. 91980) *J. Immunol.,* 124, pp. 2442–2450.
4. Cummings, R. D. and Nyame, A. K., (1996) *FASEB J.* 10, pp. 838–848.
5. de Jonge, N., Polderman, A. M., Hilberath, G. W., Krijger, F. W. and Deelder. A.<. (1990) *Trop. Med. Parasitol.* 41, pp. 257–261.
6. DeBose-Boyd, R., Nyame, A. K., Cummings, R. D., (1996) *Exp. Parasitol.,* 82, pp. 1–10.
7. Deelder, A. M., Kornelis, D., Van Marck, E. A. E., Eveleigh, P. C. and Van Egmond, J. G. (1980) *Exp. Parasitol.,* 50, pp. 16–32.
8. Kang, S., Cummings, R. D., and McCall, J. W., (1993) *J. Parasitol.,* 79, pp. 815–828.
9. Li, F., Erickson, H. P., James, J. A., Moore, K. L., Cummings, R. D., and McEver, R. P., (1996) *J. Biol. Chem.,* 271, pp. 6342–6348.
10. Moore, K. L., Patel, M. D., Breuhl, R. E., Fugang, L., Johnson, D. A., Lichenstein, H. s., Cummings, R. D., Bainton, D. F. and McEver, R. P. (1995) *J. Cell Biol.,* 128, pp. 661–671.
11. Nash, T. E., (1978) *Am. J. Trop. Med. Hvq.,* 27, 939–943.
12. Nash, T. E., and Deedler, A. M. (19850 *Am. J. Trop. Med. Hvq.,* 34, pp. 236–241.
13. Nash, T. E., Nasir, U. -D., and Jeanloz, R. W., (1977) *J. Immunol.,* 119, pp. 1627–1633.
14. Nash, T. E., Ottensen, E. A. and Cheever, A. W., (1978) *Am. J. Trop. Med. Hvq.,* 27, pp. 944–950.
15. Nayme, A. K., Pilcher, J. B., Tsang, V. C. W., and Cummings, R. D., (1997) *Glycobiology,* 7, pp. 2076–216.
16. Nyame, A. K., Pilcher, J. B., Tsang, V. C. W., and Cummings, R. D. (1996), *Exp. Parasitol.* 82, pp. 191–200.
17. Nyame, K., Cummings, R. D. and Damia, R. T., (1987) *J. Biol. Chem.,* 262, pp. 7990–7995.
18. Nyame, K., Cummings, R. D., and Damian, R. T., (1988a), *J. Parasitol.,* 74, pp. 562–572.
19. Nyame, K., Cummings, R. D., and Damian, R. T., (1988b), *Mol. Biochem. Parasitol.,* 28, pp. 265–274.
20. Nyame, K., Smith, D. F., Damian, R. T., and Cummings, R. D., (1989), *J. Biol. Chem.,* 264, pp. 3235–3243.
21. Srivatsan, J., Smith, D. F., and Cummings, R. D., (1992a), *J. Biol. Chem.,* 267, pp. 20196–20203.
22. Srivatsan, J., Smith, D. F. and Cummings, R. D., (1992b), *Glycobiology,* 2, pp. 445–452.
23. Srivatsan, J., Smith, D. F., and Cummings, R. D., 91994), *J. Parasitol.,* 80, pp. 884–890.
24. van Dam, G. J., Bergwerff, A. A., Thomas-Oates, J. E., Rotsmans, J. P., Kamerling, J. P., Vliegenthart, J. F. G., and Deelder, A. M., (1994) *Eur. J. Biochem.* 225, pp. 467–482.
25. van Lieshout, L., Panday, U. G., de Jonge, N. Krijger, F. W., Oostburg, B. F., Polderman, A. M. and Deelder, A. M., (1995) *Acta Trop.,* 59, pp. 19–29.
26. van Lieshout, L., Polderman, A. M., Visser, L. G., Verwey, J. J., and Deelder, A. M., (1997) *Trop. Med. Int. Health,* 2, pp. 551–557.
27. Van't Wout, A. B., De Jonge, N., Wood, S. M., Van Lieshout, L., Mitchell, G. F. and Deelder, A. M., (1995) *Parasitol. Res.,* 81, 434–437.
28. Yan, L., Alvarez-Manilla, G., Smith, D. F., Cummings, R. D., (1996) *Glycoconj. J.,* 14, pp. 45–56.

What is claimed is:

1. A kit for diagnosing a parasitic helminth infection in a human and distinguishing a Schistosoma infection from a non-Schistosoma helminth infection, comprising;

a first reagent for detecting a helminth antigen characteristic of both Schistosoma and other parasitic helminths wherein the helminth antigen is at least one of GalNAcβ1→4GlcNAc-R(LDN) and GalNAcβ1→4[Fucα1→3]GlcNAc-R (LDNF); and a second reagent for detecting a Schistosoma antigen characteristic of Schistosoma species which is not found in other parasitic helminths wherein the Schistosoma antigen is Galβ1→4[Fucα1→3]GlcNAc-R ($Le^x$).

* * * * *